(12) United States Patent
Campbell, Jr.

(10) Patent No.: US 10,159,255 B2
(45) Date of Patent: Dec. 25, 2018

(54) BIOCIDAL GLAZING COMPOSITION, METHOD, AND ARTICLE

(71) Applicant: Microban Products Company, Huntersville, NC (US)

(72) Inventor: Alvin Lamar Campbell, Jr., Huntersville, NC (US)

(73) Assignee: Microban Products Company, Huntersville, NC (US)

( * ) Notice: Subject to any disclaimer, the term of this patent is extended or adjusted under 35 U.S.C. 154(b) by 398 days.

(21) Appl. No.: 14/962,838

(22) Filed: Dec. 8, 2015

(65) Prior Publication Data

US 2016/0081349 A1 Mar. 24, 2016

Related U.S. Application Data

(60) Provisional application No. 62/089,957, filed on Dec. 10, 2014.

(51) Int. Cl.
| | | |
|---|---|---|
| *B32B 15/04* | (2006.01) | |
| *A01N 59/20* | (2006.01) | |
| *A01N 59/16* | (2006.01) | |
| *C04B 41/86* | (2006.01) | |
| *A01N 25/34* | (2006.01) | |
| *C03C 8/14* | (2006.01) | |
| *C03C 8/20* | (2006.01) | |
| *C04B 33/34* | (2006.01) | |
| *C04B 41/00* | (2006.01) | |
| *C04B 41/50* | (2006.01) | |
| *C04B 111/20* | (2006.01) | |

(52) U.S. Cl.
CPC ............ *A01N 59/20* (2013.01); *A01N 25/34* (2013.01); *A01N 59/16* (2013.01); *C03C 8/14* (2013.01); *C03C 8/20* (2013.01); *C04B 33/34* (2013.01); *C04B 41/009* (2013.01); *C04B 41/5022* (2013.01); *C04B 41/86* (2013.01); *C03C 2204/02* (2013.01); *C04B 2111/2092* (2013.01)

(58) Field of Classification Search
USPC ................ 428/688, 689, 697, 701, 702
See application file for complete search history.

(56) References Cited

U.S. PATENT DOCUMENTS

| | | | |
|---|---|---|---|
| 5,304,516 A | 4/1994 | Clifford | |
| 5,348,797 A * | 9/1994 | Clough | B05D 5/12 |
| | | | 428/323 |
| 5,597,644 A * | 1/1997 | Araki | B82Y 25/00 |
| | | | 156/89.16 |
| 5,807,641 A * | 9/1998 | Oku | C03C 8/14 |
| | | | 428/428 |
| 5,853,866 A | 12/1998 | Watanabe et al. | |
| 5,882,808 A | 3/1999 | Oku et al. | |
| 6,043,171 A | 3/2000 | Siebers et al. | |
| 6,143,318 A * | 11/2000 | Gilchrist | A61K 33/22 |
| | | | 424/404 |
| 6,303,183 B1 | 10/2001 | Wilczynski et al. | |
| 6,368,668 B1 | 4/2002 | Kobayashi et al. | |
| 6,383,646 B1 | 5/2002 | Tomioka et al. | |
| 6,514,622 B1 | 2/2003 | Hayakawa et al. | |
| 6,756,060 B1 | 6/2004 | Greenspan et al. | |
| 6,887,812 B2 | 5/2005 | Nenasheva et al. | |
| 7,250,178 B2 | 7/2007 | Olsson et al. | |
| 7,476,698 B2 | 1/2009 | Wagener et al. | |
| 7,488,442 B2 | 2/2009 | Matsumoto et al. | |
| 9,758,428 B1 * | 9/2017 | Zhang | C03C 21/005 |
| 2003/0134107 A1 | 7/2003 | Machida et al. | |
| 2004/0103823 A1 | 6/2004 | Kurihara et al. | |
| 2005/0031703 A1* | 2/2005 | Beier | A01N 59/16 |
| | | | 424/601 |
| 2005/0035500 A1 | 2/2005 | Matsumoto et al. | |
| 2005/0106336 A1 | 5/2005 | Ong et al. | |
| 2005/0158400 A1 | 7/2005 | Olsson et al. | |
| 2005/0196430 A1 | 9/2005 | Olsson et al. | |
| 2005/0249791 A1 | 11/2005 | Hobbs et al. | |
| 2005/0252410 A1 | 11/2005 | Bujard et al. | |

(Continued)

FOREIGN PATENT DOCUMENTS

| | | |
|---|---|---|
| CA | 2279785 A1 | 2/2000 |
| CN | 1615698 A | 5/2005 |

(Continued)

OTHER PUBLICATIONS

International Search Report and Written Opinion of corresponding application PCT/US2015/064634, dated Feb. 16, 2016, all enclosed pages cited.
Supplementary Partial European Search Report; European Application EP 08730070, dated May 15, 2015; all enclosed pages cited.
Supplementary Partial European Search Report; European Application EP 08730070, dated Oct. 5, 2015; all enclosed pages cited.
Enamel; 9th Edition of Encyclopedia Britannica—free ninth edition online encyclopedia Britannica; vol. 8; all enclosed pages cited.
PCT International Search Report and Written Opinion; PCT/US2008/054190; dated Jun. 30, 2008; all enclosed pages cited.
AATCC Committee RA31, "AATCC Test Method 100-1999, Antibacterial Finishes on Textile Materials: Assesment of", AATCC Technical Manual, 2003, pp. 149-151.

(Continued)

*Primary Examiner* — Lauren R Colgan
(74) *Attorney, Agent, or Firm* — Nelson Mullins Riley & Scarborough LLP

(57) ABSTRACT

A biocidal additive package comprises at least one metal or metal containing compound selected from the group consisting of $Cu_2O$, $Cu(OH)_2$, $Cu$, $CuO_3$, $Cu_2O_3$, and a combination thereof, and at least one non-copper metal or non-copper containing metal compound. Non-limiting examples of non-copper metal and non-copper containing metal compounds are Ag, $Ag_2O$, Bi, $Bi_2O_3$, Zn, ZnO, or a combination thereof. A biocidal ceramic glaze layer and an article comprising a biocidal ceramic glaze layer are provided. Also provided is a method of affixing a biocidal ceramic glaze to a substrate.

10 Claims, No Drawings

(56) References Cited

U.S. PATENT DOCUMENTS

| | | |
|---|---|---|
| 2006/0048676 A1 | 3/2006 | Bujard |
| 2006/0141015 A1* | 6/2006 | Tessier .................. A01N 59/16 424/443 |
| 2007/0110824 A1 | 5/2007 | Nageswaran |
| 2007/0275168 A1 | 11/2007 | Prochazka |
| 2008/0085326 A1* | 4/2008 | Ruan ...................... A61K 33/00 424/618 |
| 2009/0104459 A1* | 4/2009 | Campbell, Jr. ..... C04B 41/5022 428/446 |
| 2009/0117173 A1 | 5/2009 | Chen et al. |
| 2010/0204411 A1* | 8/2010 | Erneta ................... A01N 59/16 525/415 |
| 2012/0237686 A1 | 9/2012 | Chen et al. |
| 2013/0302440 A1* | 11/2013 | King ...................... A01N 59/16 424/618 |
| 2014/0212361 A1* | 7/2014 | Ijaz ........................ A01N 59/20 424/45 |
| 2014/0220153 A1 | 8/2014 | Pagotto Simões et al. |
| 2014/0271757 A1* | 9/2014 | Agrawal ................ A61K 33/34 424/405 |
| 2014/0356406 A1* | 12/2014 | Patil ...................... A01N 25/04 424/411 |
| 2015/0030696 A1 | 1/2015 | Campbell, Jr. |
| 2015/0030861 A1 | 1/2015 | Campbell, Jr. |
| 2015/0030863 A1 | 1/2015 | Campbell, Jr. |
| 2015/0099095 A1* | 4/2015 | Pershin .................. A01N 59/20 428/141 |
| 2015/0359946 A1* | 12/2015 | Dehnad .................. A61L 29/16 424/411 |
| 2016/0135470 A1* | 5/2016 | Agrawal .................. A61K 8/25 424/404 |
| 2016/0143291 A1* | 5/2016 | Campbell, Jr. ........ A01N 59/16 424/618 |
| 2017/0231229 A1* | 8/2017 | Meier ................. C23C 14/0641 424/409 |

FOREIGN PATENT DOCUMENTS

| | | |
|---|---|---|
| CN | 1843995 A | 10/2006 |
| DE | 19834801 A1 | 2/2000 |
| DE | 202005006784 U1 | 9/2005 |
| EP | 0190504 A2 | 8/1986 |
| JP | H08290985 A | 11/1996 |
| JP | H111380 A | 1/1999 |
| WO | 2000/014029 | 3/2000 |
| WO | 2004092283 A2 | 10/2004 |

OTHER PUBLICATIONS

Levin, Ernest M., Robbins, Carl R. and McMurdie, Howard F., "Phase Diagrams for Ceramists", Compiled at the National Bureau of Standards, 1964, The American Ceramic Society, pp. 69 and 120, Columbus, Ohio.

Oliveira, Herbert V., et al., "Manual of Drying and Firing Porclain Enamel", PEI-601, Version 1.2, Porcelain Enamel Institute, copyright 1996-1997, Nashville, Tennessee, pp. 1-22.

Japanese Minister of International Trade and Industry and the Japanese Industrial Standards Committee, "Antimicrobial products—Test for antimicrobial activity and efficacy", Japanese Standards Association, reference No. JIS Z 2801: 2000(E), published Dec. 20, 2000, Tokyo, Japan, pp. 1-11.

Eppler, Richard A. and Obstler, Mimi, "Understanding Glazes", The American Ceramic Society, Westerville, Ohio, 2005, pp. 246, 247, 315.

ASTM International Designation: C286, "Standard Terminology Relating to Porcelain Enamel and Cermic-Metal Systems", ASTM International, 1999 (reapproved 2009), published Jan. 2010, West Conshohocken, P.A., pp. 1 and 4.

The Edward Orton Jr. Ceramic Foundation, "Temperature Equivalent Chart for Orton Pyrometric Cones (C)", www.ortonceramic.com, 2011.

ASTM International Designation: C 347-57 (reapproved 1983), "Standard Test Method for Reflectance, Reflectivity, and Coefficient of Scatter of White Porcelain Enamels", ASTM International, Annual Book of Standards, vol. 14.02, Dec. 1983, pp. 733-735.

\* cited by examiner

BIOCIDAL GLAZING COMPOSITION, METHOD, AND ARTICLE

CROSS-REFERENCE TO RELATED APPLICATIONS

This application claims priority from U.S. Provisional Patent Application No. 62/089,957, filed on Dec. 10, 2014, and from U.S. patent application Ser. Nos. 13/931,805, 13/931,808 and 13/931,810, each filed on Jun. 28, 2013, which are divisionals of U.S. patent application Ser. No. 12/032,657, filed on Feb. 16, 2008, in the United States Patent and Trademark Office. The disclosures of which are incorporated herein by reference in their entireties.

FIELD OF THE INVENTION

The present invention relates to the field of biocidal protection in a ceramic or porcelain glaze layer on a substrate. More specifically, the present invention relates to a biocidal composition and method for use suitable for imparting built-in and long lasting biocidal characteristics to a glazed article.

BACKGROUND OF THE INVENTION

An area of particular commercial interest is ceramic articles and ceramic coatings. Ceramic coatings are commonly used in products that store, treat, or transport water and liquid waste. Ceramic toilets, urinals, bidets, bathroom basins (collectively known as sanitary ware), flooring tiles and other bathroom fixtures are probably the most common example of such products.

Ceramic glaze layers further are commonly affixed to tiles and other articles used for wall tiling. In this product application, the tiles typically are larger and the glaze layer significantly thinner than floor tiles.

Ceramic products often become stained by scum and films of biologic origin (e.g., bacteria, fungus, mold, mildew). To date, the primary method of removing biological scum and film from these ceramic products has been to abrade the ceramic surface in the presence of a topical cleaning agent.

Generally, ceramic glaze compositions are unpredictably sensitive to the introduction of metallic additives, the latter frequently causing negative structural and/or aesthetic consequences in a fired glaze. In view of this fact, a person having ordinary skill in the ceramic art reasonably would expect the introduction of additional metallic compounds into a ceramic glaze base to negatively affect any one or more of the pre-fired physical properties of the ceramic glazing composition; the parameters of the firing process; and most critically, the structure of the fired glaze layer and/or the desired biocidal effect.

Wall tile applications typically employ a thin glaze layer as compared to ceramic glazed tiles intended for use in flooring or countertops: on the order of about 5-15 um as compared to about 100 um for floor tile. Thin-layer ceramic glazing compositions in particular are exquisitely susceptible to the above technical challenges.

There is a need for a thin-layer ceramic glazing composition that can impart built-in protection against the growth and proliferation of microbes to a fired glaze layer formed therefrom. However, existing technologies are somewhat limited in this regard. For example, the high temperatures used in ceramic firing processes typically preclude the use of organic biocidal agents.

At efficacious levels, conventional inorganic silver-based antibacterial compounds (e.g., zeolite, amorphous glass, sol-gel) generally are too expensive for commercial use. Moreover, incorporation of silver-based biocidal agents into ceramic glazes routinely presents issues of clouding, crazing, discoloration, and other undesirable consequences to the glaze aesthetics.

Zinc oxide is known as having biocidal characteristics and has been used in the preparation of ceramic glazing compositions. However, known ceramic glazing compositions that rely solely upon zinc oxide as a biocidal agent have not shown biocidal efficacy sufficient for control of microbial growth and proliferation on ceramic surfaces. High levels of zinc-based additives—that is, at levels high enough to confer a durable biocidal property to the glaze layer—further cause clouding, opacity, marbling, or other negative optical effects in the glaze layer, rendering them unsuitable for use in commercial products. Zinc also is incompatible with some segments of the glaze color palette.

Accordingly, there is a need for a thin-layer ceramic coating that offers persistent built-in biocidal protection while being aesthetically and optically neutral.

SUMMARY OF THE INVENTION

The present invention relates to a biocidal additive package comprising at least one metal or metal containing compound selected from the group consisting of $Cu_2O$, $Cu(OH)_2$, $Cu$, $CuO_3$, $Cu_2O_3$, and a combination thereof, and at least one non-copper metal or non-copper containing metal compound.

In another embodiment, a ceramic glaze layer is provided. The ceramic glaze layer comprises at least one metal or metal containing compound selected from the group consisting of $Cu_2O$, $Cu(OH)_2$, $Cu$, $CuO_3$, $Cu_2O_3$, and a combination thereof, and at least one non-copper metal or non-copper containing metal compound.

In another embodiment, a method of affixing a biocidal ceramic glaze to a substrate is provided. The method comprises providing a biocidal ceramic glazing composition having one or more biocidal agents disposed therein, applying the biocidal ceramic glazing composition to a substrate having a surface, wherein the biocidal ceramic glazing composition comprises at least one metal or metal containing compound selected from the group consisting of $Cu_2O$, $Cu(OH)_2$, $Cu$, $CuO_3$, $Cu_2O_3$, and a combination thereof, and at least one non-copper metal or non-copper containing metal compound.

In another embodiment, a biocidal ceramic article is provided. The biocidal ceramic article comprises a substrate and a ceramic glaze layer on the substrate. The ceramic glaze layer comprises at least one metal or metal containing compound selected from the group consisting of $Cu_2O$, $Cu(OH)_2$, $Cu$, $CuO_3$, $Cu_2O_3$, and a combination thereof, and at least one non-copper metal or non-copper containing metal compound.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

DETAILED DESCRIPTION OF THE INVENTION

As used herein, the terms "microbe" or "microbial" should be interpreted to refer to any of the microscopic organisms studied by microbiologists or found in the use environment of a ceramic article or ceramic-glazed article. Such organisms include, but are not limited to, bacteria and fungi as well as other single-celled organisms such as mold, mildew and algae. Viral particles and other infectious agents are also included in the term microbe.

As well, "biocidal" and like terms should be interpreted as encompassing both microbe-killing as well as microbistatic activities. That is, it herein is considered efficacious if a biocidal composition reduces the number of microbes on a substrate or it the composition retards the normal rate of microbial growth.

For ease of discussion, this description uses the terms microbes and biocidal to denote a broad spectrum activity (e.g. against bacteria and fungi). When speaking of efficacy against a particular microorganism or taxonomic rank, the more focused term will be used (e.g. antifungal to denote efficacy against fungal growth in particular).

Using the above example, it should be understood that efficacy against fungi does not in any way preclude the possibility that the same biocidal composition demonstrates efficacy against another class.

For example, discussion of the strong bacterial efficacy demonstrated by a disclosed embodiment should not be read to exclude the embodiment from also demonstrating antifungal activity. This method of presentation should not be interpreted as limiting the scope of the invention in any way.

A first embodiment is a biocidal additive package adapted for use in a ceramic glazing composition, the latter being useful in the formation of a thin-layer ceramic layer on a substrate. The biocidal additive package comprises one or more metal or metal-based compounds.

A second embodiment disclosed herein is a ceramic glazing composition adapted for use in the formation of a thin-layer ceramic layer on a substrate, wherein the glazing composition contains a biocidal additive package including one or more metal or metal-based compounds.

A third embodiment is a method for forming a glaze layer on a substrate, the method including the step of applying a biocidal additive package to an unfired substrate surface (either as a component of a glazing composition applied to the surface, or separately added/applied). The fired glazing composition yields a fired glaze layer having an insubstantial alteration of physical and aesthetic characteristics compared to an equivalent method performed using an untreated (i.e., unadulterated and non-biocidal) ceramic glazing composition.

A fourth embodiment comprises a substrate having a fired glaze layer on a first surface thereof, wherein the fired glaze layer contains oxide compounds corresponding to the metal-based compound(s) in the biocidal additive package. The fired glaze layer possesses durable biocidal properties and with insubstantial alteration of physical and aesthetic characteristics compared to an equivalent layer formed using an untreated (i.e., unadulterated and non-biocidal) ceramic glazing composition.

A fifth embodiment is an article having disposed on a surface thereof a fired glaze layer, wherein the fired glaze layer contains oxide compounds corresponding to the metal or metal-based compound(s) in the biocidal additive package. The article's fired glaze layer possesses durable biocidal properties and with insubstantial alteration of physical and aesthetic characteristics compared to an article having an equivalent layer formed using an untreated (i.e., unadulterated and non-biocidal) ceramic glazing composition.

Provided as an aid to the reader is the following brief discussion of ceramic coatings generally and, in particular, of ceramic glazing on the outer surfaces of ceramic products as well as of vitreous china or ceramic production. This discussion is presented in the context of the production of generic wall tile. Those skilled in the art will recognize that the production process of ceramic products may vary from that which is presented below, and that the ceramic glazing composition and process disclosed herein is adaptable to other substrates (e.g. sanitaryware).

Glazes are generally made from powdered glass combined with colored oxides using such elements as cobalt, chrome, manganese, or nickel. The powder mixture is suspended in water and applied to the ceramic surface by spraying, brushing, dipping, or other known application methods. For thin-layer ceramic glazing, the glazing composition is applied by serigraphy, airbrush, threading die, or bell on a traditional substrate.

The suspension, or slip, in which the glaze is applied to the ceramic surface must have particular properties to ensure that the glaze is easily applied, does not run, pool or otherwise become uneven during firing, and adheres well both when wet and after firing to ensure that the application surface remains fully wetted and covered. These slip properties often can be obtained by adding a small amount of clay to the suspension as well as by controlling both the amount of water in the slip as well as the size of the powder particles. Organic surface-active agents (e.g. surfactants, detergents) also can be added to the slip to regulate its properties.

Colors in glazes are controlled by adding coloring agents to the glassy components of the glaze. Special effects in glazes can also be produced. If salt is added to the kiln during firing, the glaze develops a fine orange-peel texture, which can be uniform or spotty depending upon conditions. A glaze that froths during firing gives a rough surface of broken bubbles known as a blister glaze.

Turning now to the biocidal composition and biocidal ceramic glazing composition it is adapted for use in, it first was undertaken to identify a baseline glaze composition— that is, a conventional, non-biocidal ceramic glaze base— and methodology to aid in identification of suitable and efficacious biocidal agents. A conventional glaze was chosen as the base glaze for sample trials based on its fairly representative composition and the lack of metals contained in the inventive biocidal combinations tested herein.

The conventional glaze composition used for experimental trials herein is composed of 95% slow-fire base glaze (containing primarily $SiO_2$ and secondarily, inter alia, KNaO, CaO, BaO, $SrOAl_2O_3$ or $B_2O_3$).

Alkaline earth oxide materials such as calcium carbonate, wollastonite, and zinc oxide are generally added as raw materials. Other alkaline earth oxides such as lead oxide, strontium oxide, barium oxide, and magnesium oxide are more typically added in a fritted form. The alkaline earth oxides are advantageous because they provide fluxing action without having a major effect on glaze thermal expansion. Oxides also can serve as coloring compounds.

Also resident in the glaze composition is 5% EPK kaolin, and an over-addition of 1% bentonite (absorbent aluminum silicate clay formed from volcanic ash and well known to those of skill in the ceramic art). This dry material is blended into a sufficient quantity of de-ionized water to produce a glaze slip with a specific gravity of 1.35±0.05 g/cc. This represents a solids content of 41.74%.

A biocidal glazing composition was made by adding together (e.g. by mixing) conventional glazing composition components and biocidal agent combinations, preferably in the form of a biocidal additives package.

The biocidal additive package contains one or more metal-containing compounds. In an aspect of the invention, at least one metal or metal-containing compound contains copper. Notable copper-containing metal compounds include, but are not limited to: copper (II) oxide (CuO) (CAS No. 1317-38-0), copper (I) oxide ($Cu_2O$) (CAS No. 1317-39-1), copper hydroxide ($Cu(OH)_2$) (CAS No. 20427-59-2), metallic copper (Cu) (CAS No. 7440-50-8), copper carbonate ($CuCO_3$) (CAS No. 471-34-1), and copper (III) oxide ($Cu_2O_3$).

In another aspect of the invention, the biocidal additive package may contain one or more non-copper containing metal compounds as possible biocidal agents, alone or in addition to copper-containing metal compounds. Other possible non-copper containing metal compounds include, but are not limited to: silver-containing compounds, such as Ag, AgO (CAS No. 1301-96-8), $Ag_2O$ (CAS No. 20667-12-3), $Ag_2CO_3$ (CAS No. 534-16-7); $AgNO_3$ (CAS No. 7761-88-8); barium-containing compounds, such as $BaCO_3$ (CAS No. 513-77-9); bismuth-containing compounds, such as $Bi_2O_3$ (CAS No. 1304-76-3); tin-containing compounds, such as $SnO_2$ (CAS No. 18282-10-5); titanium-containing compounds, such as $TiO_2$ (anatase; CAS No. 13463-67-7); and zinc-containing compounds, such as ZnO (CAS No. 1314-13-2).

In another aspect of the invention, the biocidal additive package comprises a synergistic metal-containing additive combination. The synergistic additive combination may comprise copper-containing compounds, non-copper containing compounds, or a combination thereof. A non-limiting example of a synergistic additive combination comprising copper and non-copper containing compounds is a combination of $Ag_2O$, $Bi_2O_3$, ZnO and CuO.

The components and biocidal agent(s) were added based on weight of the solids content of the glaze base, excluding such biocidal agent(s). In an aspect of the invention, at least one metal-based compound is present in the ceramic glaze base in a range of 0.1 weight % to 10 weight %. The glaze base is described in greater detail above.

In preferred embodiments, the copper-containing metal compound can be present in the ceramic glaze base in a range of 1-10 weight %. The balance of the formula is carrier or vehicle for the compounds.

If used, zinc-containing compounds preferably are present in the ceramic glaze base in a range of 1-10 weight %. Silver-containing compounds, if used, preferably are present in the ceramic glaze base in a range of 0.1-3.0 weight %.

The glaze base, with biocidal agent(s) admixed therein, then ball milled for at least fifteen minutes. The milled glaze base was held overnight to allow for hydration, and then remixed. The biocidal glazing composition then was ready to be applied to a substrate (e.g. a bisque tile).

All material addition calculations are based upon the percent solids of the baseline glaze and the specific gravity is checked before each group of material evaluation samples is processed. Each material to be evaluated was added to 1000 milliliters (1 Liter) of base glaze.

It is expected, however, that other conventional ceramic glaze compositions could be substituted without departing from the essential features of the biocidal ceramic glaze as described herein.

A method of affixing a ceramic glaze to a substrate confers durable biocidal properties to the substrate. The method generally comprises providing a ceramic glazing composition having one or more biocidal agents disposed therein as set forth in the present disclosure, applying the biocidal glazing composition to a substrate, and curing the glazing composition in accordance with conventional glaze-firing techniques.

Development work utilized dipping to apply the glaze formulation to tiles, although other methods of application known to those in the art may be used. Alternative techniques for applying a glazing composition to a substrate include, without limitation: rolling, pouring, brushing, sponging, spraying, atomizing, and the like. The glaze is then dried and fixed onto the ceramic surface by firing.

During firing, the powdered glass softens and largely equilibrates over the surface, reacting with the substrate to form a strong, adherent union therewith. A glazing composition typically is applied to an unfired substrate surface.

Alternatively, the glazing composition may be applied to an already fired glaze layer on the substrate surface. In this latter instance, a second firing is necessary to melt and bond the glazing composition to the first glaze layer.

As a second alternative, the glazing composition can be applied to the surface of an unfired first glazing composition on the substrate surface, with the substrate and both glazing compositions fired together in one firing step. The biocidal additive package can be applied to the surface of an unfired substrate independent of the application of a ceramic glazing composition.

Various components, such as alkali oxide, borates, and lead oxide, can be added to the ceramic glaze composition to facilitate softening at lower temperatures in order that the glaze flow more easily during firing and to minimize roughness and defects in the fired ceramic glaze surface. The present biocidal combinations are compatible with these common additives.

Another application method involves delivery to the glazed surface, by any of the methods enumerated previously, of antimicrobial components suspended in a carrier or vehicle (e.g. water, polyethylene glycol). The antimicrobial components are blended in the proper ratios and then suspended in a vehicle or carrier prior to application. The applied amount of antimicrobial is simply the ratio of the percent solids of antimicrobial components versus the amount of the carrier. The applied antimicrobial coating will be incorporated into the surface of the glaze during the firing operation.

The glazing step typically comprises the application of ceramic glaze on the parts using guns in individual booths fitted with exhaust systems and water curtains. Typical ceramic glaze is produced from a mixture of kaolin, feldspar, quartz, colorings and other additives. Once coated, the parts are fired in continuous kilns, reaching temperatures up to about 1270° C. in an approximately 15-hour cycle.

The firing process gives the glazed part the color and transparent appearance that is typical of vitreous china.

The procedure to manufacture samples for material evaluation was straightforward. A reservoir of baseline glaze was applied on or to sample tiles by dipping or spraying, resulting in a coated tile.

Coated tiles were placed into a tile sagger, each sagger capable of holding up to twenty tiles. The sagger was placed into one of the two electric kilns or a gas-fired kiln and fired. The firing profiles tested ranged from Pyrometric Cone Equivalent 06 ("Cone 06") to Cone 8, using Orton Large (regular) cones at 270° F./hr (150° C./hr). Baseline (untreated) glaze samples were fired at temperatures ranging from about 1850° F./1010° C. (Cone 06) to about 2315° F./1270° C. (Cone 8).

For reference, the relevant Orton Cone temperature data is presented in Tables 1-2.

TABLE 1

| Cone | Self-Supporting (Reg.) | | | Large (Reg.) | | Small (Reg.) |
|---|---|---|---|---|---|---|
| | 27° F. per hr | 108° F. per hr | 270° F. per hr | 108° F. per hr | 270° F. per hr | 540° F. per hr |
| 07 | 1764 | 1789 | 1809 | 1783 | 1805 | 1846 |
| 06 | 1798 | 1828 | 1855 | 1823 | 1852 | 1873 |
| 05½ | 1839 | 1859 | 1877 | 1854 | 1873 | 1909 |
| 05 | 1870 | 1888 | 1911 | 1886 | 1915 | 1944 |
| 04 | 1915 | 1945 | 1971 | 1940 | 1958 | 2008 |
| 03 | 1960 | 1987 | 2019 | 1987 | 2014 | 2048 |
| 02 | 1972 | 2016 | 2052 | 2014 | 2048 | 2098 |
| 01 | 1999 | 2046 | 2080 | 2043 | 2079 | 2152 |
| 1 | 2028 | 2079 | 2109 | 2077 | 2109 | 2163 |
| 2 | 2034 | 2088 | 2127 | 2088 | 2124 | 2174 |
| 3 | 2039 | 2106 | 2138 | 2106 | 2134 | 2185 |
| 4 | 2086 | 2124 | 2161 | 2120 | 2158 | 2208 |
| 5 | 2118 | 2167 | 2205 | 2163 | 2201 | 2230 |
| 5½ | 2133 | 2197 | 2237 | 2194 | 2233 | N/A |
| 6 | 2165 | 2232 | 2269 | 2228 | 2266 | 2291 |
| 7 | 2194 | 2262 | 2295 | 2259 | 2291 | 2307 |
| 8 | 2212 | 2280 | 2320 | 2277 | 2316 | 2372 |
| 9 | 2235 | 2300 | 2336 | 2295 | 2332 | 2403 |

The above procedure approximates a conventional thin-layer glaze application in a production environment. The final baseline glaze formulations resulted in samples having a glassy surface at ambient temperature, highly resistant to absorption of dyes, and exhibiting no biocidal properties.

Microscopic imaging of the baseline glaze/tile interface revealed complete vitrification of the glaze with no inclusions of bubbles or unmelted materials. The baseline samples are the foundation for comparing and judging the candidate materials. The adopted baseline glaze is simple in composition, easy to process and apply, and has a conventional firing temperature. These attributes greatly facilitated the evaluation of candidate material samples.

TABLE 2

| Cone | Self-Supporting (Reg.) | | | Large (Reg.) | | Small (Reg.) |
|---|---|---|---|---|---|---|
| | 15° C. per hr | 60° C. per hr | 150° C. per hr | 60° C. per hr | 150° C. per hr | 300° C. per hr |
| 07 | 962 | 976 | 987 | 973 | 985 | 1008 |
| 06 | 981 | 998 | 1013 | 995 | 1011 | 1023 |
| 05½ | 1004 | 1015 | 1025 | 1012 | 1023 | 1043 |
| 05 | 1021 | 1031 | 1044 | 1030 | 1046 | 1062 |
| 04 | 1046 | 1063 | 1077 | 1060 | 1070 | 1098 |
| 03 | 1071 | 1086 | 1104 | 1086 | 1101 | 1131 |
| 02 | 1078 | 1102 | 1122 | 1101 | 1120 | 1148 |
| 01 | 1093 | 1119 | 1138 | 1117 | 1137 | 1178 |
| 1 | 1109 | 1137 | 1154 | 1136 | 1154 | 1184 |
| 2 | 1112 | 1142 | 1164 | 1142 | 1162 | 1190 |
| 3 | 1115 | 1152 | 1170 | 1152 | 1168 | 1196 |
| 4 | 1141 | 1162 | 1183 | 1160 | 1181 | 1209 |
| 5 | 1159 | 1186 | 1207 | 1184 | 1205 | 1221 |
| 5½ | 1167 | 1203 | 1225 | 1201 | 1223 | N/A |
| 6 | 1185 | 1222 | 1243 | 1220 | 1241 | 1255 |
| 7 | 1201 | 1239 | 1257 | 1237 | 1255 | 1264 |
| 8 | 1121 | 1249 | 1271 | 1247 | 1269 | 1300 |
| 9 | 1224 | 1260 | 1280 | 1257 | 1278 | 1317 |

In production, this fired glaze layer is of a thickness that is commonly used in the ceramics and sanitaryware industries, which is generally, 0.3 mm to 2.0 mm in thickness. A second method of producing a biocidal surface would entail use of a secondary glaze applied over the regular (first) glaze. This glaze thickness optionally could be 0.5 millimeters or less in thickness.

It is expected that exposure of the glazed tile to microbes will result in microbial contact only with the glazed composition on the surface of the glazed tile. Material below the surface is trapped within the glass of the glaze and thereby sequestered from microbes.

A variety of biocidal agents were tested in the baseline glaze composition after glazing of a substrate sample. Of these compounds, a variety of combinations also were assessed, as detailed in the following discussion and examples.

A ceramic article bearing the above-described biocidal glaze composition exhibits durable biocidal properties. The biocidal ceramic article comprises a substrate, for example a ceramic substrate, having at least a first surface; and a fired or cured glaze disposed on at least a portion of the first surface. The ceramic glazing composition utilized in this embodiment is the same as that described previously.

Pre-fired physical properties of the ceramic glazing composition—the presence of a new additive, such as metallic oxides and salts, can unpredictably change the character of the glazing composition, resulting in altered flowability, foaming, and/or sedimentation.

The biocidal ceramic glaze was designed to impart durable (persistent) and built-in biocidal protection to a variety of ceramic articles. Accordingly, the scope of the disclosure includes ceramic articles that incorporate the present biocidal glazing. Such articles include, but are not limited to, toilets, bidets, washbasins, towel rails, soap holders, toilet roll holders, water control fixtures (e.g., hot and cold water handles), ceramic glazed tiles (e.g. floor tile, wall tile), sculptures, and other articles.

EXAMPLES

Example 1

Ceramic Evaluation of Antimicrobial Materials

In a first example, biocidal agents were used to manufacture a range of biocidal glaze compositions, each composition consisting of one or more biocidal agents. Several ceramic articles then were prepared to test the biocidal characteristics of the recited glazes. The test articles comprised an underlying ceramic substrate made from a standard commercial barbotine.

The glaze used in the testing was the baseline glaze described previously, to which was added varying quantities of biocidal agent combinations as noted. The glaze composition was applied to the articles by dipping, and the test articles were then fired.

As mentioned, one or more biocidal agents were assessed for biocidal efficacy in fired glazes on ceramic substrates. Copper-containing compounds were evaluated. Among the copper-containing compounds evaluated were:
$CuO$;
$Cu_2O$;
$Cu(OH)_2$;
$Cu$;
$CuCO_3$;
$Cu_2O_3$;
Combination No. 1 of: 2% $Ag_2O$, 2% $Bi_2O_3$, 2% $ZnO$, and 2% $CuO$;
Combination No. 2 of: 2% $Bi_2O_3$ and 4% $ZnO$; and
Combination No. 3 of: 2% $Ag_2O$, 2% $Bi_2O_3$, and 2% $ZnO$.

For CuO in base glaze, the additive was mixed into the base glaze and applied by spraying. For $Cu_2O$ in base glaze, the additive was mixed into the base glaze and applied by spraying. For Cu in base glaze, the additive was mixed into the base glaze and applied by spraying. For CuO in combination with another compound, CuO was mixed with water and a suspension agent and applied by spraying. An example of such suspension agent is CR1911, commercially available from Zschimmer and Schwartz, Inc. The base glaze was applied by being rolled onto the substrate.

Test articles also were prepared without any biocidal agents in the glaze for use as a negative control.

The measure of biocidal efficacy is the reduction in the number of organisms surviving the testing protocol in comparison with the baseline standard. Minimum efficacy is assumed to originate at a reduction level of 1 common logarithm (log (NOS Std/NOS Sample)).

The testing is in accordance with a modified JIS Z2801: 2000 test protocol (available from Japanese Industrial Standards Committee, Tokyo, Japan). The Z2801 protocol is an internationally known standard test for biocidal activity and efficacy. The protocol and specific modifications made thereto are summarized below.

Sample tile pieces having a diameter of approximately 55 mm were used. Ceramic glaze composition was applied and fired according to the instructions for the commercial glaze base employed. This preparation process yielded test disks having about a top surface area of about 2500 square millimeters.

Samples alternatively were made from conventional tile manufactured in factory-scale facilities. Manufactured 4-inch tiles (i.e., having 4-inch by 4-inch square dimensions) were cut into nine essentially equal square regions, with each square sub-tile having a side length of approximately 30-35 mm. These square sub-tiles were used in various testing.

The comparison test for biocidal efficacy used *Escherichia coli*, ATCC 8739 ("Ec"). The test organism was grown, and a portion of an exponentially growing culture was collected into Japanese Nutrient Broth (JNB) diluted 1/500. An inoculum was prepared at about $10^6$ colony-forming units (CFU) per milliliter by dilution with 1/500 JNB.

A sample tile was placed on moistened laboratory tissue in a culture plate, and 75 microliters of test inoculum (~0.8×10$^5$ CFU) was pipetted onto the sample surface. A cover slip or film was placed over and in contact with the inoculum to ensure uniform and substantially complete coverage of the inoculum over the sample surface. The culture plate then was incubated for 24 hours at 37° C. with humidity.

Bacteria on the sample and cover slip/film were recovered, collected into D/E Neutralizing Broth, and counted. The biocidal activity of the test samples is expressed herein as a log reduction value, as compared to the bacterial growth of the corresponding untreated (control) sample. A log reduction is expressed as log(U/B), where U is the average CFU of the test organism from the inoculum recovered in the Neutralizing Broth from the negative control (untreated) sample tile, and B is the average CFU of the test organism recovered in the Neutralizing Broth from the inoculated sample.

Results of the testing are shown in Table 3.

TABLE 3

| | | Ec | |
|---|---|---|---|
| Sample Description | Additive | Viable Organisms | Log. Red. |
| Untreated Control (mean) | n/a | 126034 | |
| CuO in Baseglaze | CuO, 3.2 g | | 2.2 |

TABLE 3-continued

| | | Ec | |
|---|---|---|---|
| Sample Description | Additive | Viable Organisms | Log. Red. |
| Cu$_2$O in Baseglaze | Cu$_2$O, 2.9 g | | 0.5 |
| Cu in Baseglaze | Cu, 2.9 g | | 1.9 |
| Combination No. 1 | [Note 1], 9.4 g | | 0.4 |
| CuO porcelain | CuO, 0.1 g | | 0.9 |

Example 2

Ceramic Evaluation of Antimicrobial Materials

In a second example, additional tests were conducted as described above. The results of the testing are shown in Table 4.

TABLE 4

| | | Ec | |
|---|---|---|---|
| Sample Description | Additive (g) | Viable Organisms | Log Red. |
| Untreated Controls (mean) | n/a | 1929123 | |
| Combination No. 2 | | | 3.9 |
| Combination No. 3 | | | 3.8 |
| CuO (3.2 g) on Baseglaze | 3.2 g | | 4.3 |
| Cu (2.9 g) on Baseglaze | 2.9 g | | 4.3 |

Example—Copper (III) Oxide Additions

In a third example, the purpose of this experiment was to evaluate the influence on efficacy of the base glaze of additions of various copper compounds. One liter of base glaze was prepared at 1.40 g/cc (43.6% solids) for each addition. Samples were prepared as set forth in Table 5.

TABLE 5

| Sample # | Base glaze (g) | CuO (g) | Total (g) |
|---|---|---|---|
| 1 | 1400 | 6.2 | 1406.2 |
| 2 | 1400 | 12.4 | 1412.4 |
| 4 | 1400 | 24.8 | 1424.8 |
| 8 | 1400 | 49.6 | 1449.6 |

Each mixture was ball milled for at least 15 minutes before dipping fired, unglazed bisque tiles into them. Tiles were fired to Cone 05 (approximately 1915° F./1046° C.). The samples were evaluated visually and by Energy-Dispersive X-Ray spectroscopy (EDX) and QMR.

The copper compounds tested included one or more of the following: Copper (II) Oxide (CuO) (Fusion); Copper (I) Oxide (Cu$_2$O) (Laguna Clay); Copper Hydroxide (Cu(OH)$_2$) (Sigma-Aldrich); Metallic copper (Cu) (Sigma-Aldrich), and Copper Carbonate (CuCO$_3$) (Fusion).

Example—Copper Additions by Delivery of Antimicrobial Components Suspended in a Carrier or Vehicle to a Glazed Surface Tests were conducted to evaluate the efficacy of Copper (Cu) compounds. The copper compounds tested included one or more of the following: Copper (II) oxide (CuO) (Fusion) and Metallic copper (Cu) (Sigma-Aldrich). The samples were made as follows:

200 grams of a 10% solids (Cu compound) in 10% CR1911 (suspension agent) and water were prepared. Samples are shown in Table 6.

TABLE 6

| Sample | 10% CR1911 in H$_2$O (g) | Cu (g) | Total (g) |
|---|---|---|---|
| CuO | 200 | 20 | 220 |
| Cu | 200 | 20 | 220 |

Each mixture was ball mixed for at least 15 minutes. Unfired bisque tiles were dipped in base glaze and left to dry overnight or for a couple of hours. Cu mixtures were then spray applied to tiles on top of dry base glaze in weight amounts as specified in Table 3. Tiles were fired to Cone 05 (approx. 1915° F./1046° C.) in the gas kiln. The tiles were examined visually, examined and tested. In this method, the Cu compounds were spray applied on top of the dried base glaze instead of being mixed into the base glaze and then spray applied as with the other application method.

RESULTS

The present invention yielded glazed surfaces that were significantly less green or lighter green in color than addition of copper conventionally has caused. In some cases, the use of a second additive (e.g. ZnO) nearly (although not completely) eliminated the greenish cast that copper addition typically introduces in a fired glazed layer. The glazed layer did not appear to suffer imperfections such as cracks, bubbles, uneven surface texture, or a milky or cloudy haze.

After firing, the glazed layer possessed a persistent biocidal property. Most advantageously, one such biocidal property is a "quick-kill" ability that is demonstrated by a 2- or 3-log reduction in bacterial growth in 2 hours as compared to the bacterial growth of a non-treated article.

It will therefore be readily understood by those persons skilled in the art that the present composition and methods are susceptible of broad utility and application. Many embodiments and adaptations other than those herein described, as well as many variations, modifications and equivalent arrangements, will be apparent from or reasonably suggested to one of ordinary skill by the present disclosure and the foregoing description thereof, without departing from the substance or scope thereof.

Accordingly, while the present composition and methods have been described herein in detail in relation to its preferred embodiment, it is to be understood that this disclosure is only illustrative and exemplary and is made merely for purposes of providing a full and enabling disclosure.

The foregoing disclosure is not intended or to be construed to limit or otherwise to exclude any such other embodiments, adaptations, variations, modifications and equivalent arrangements.

What is claimed is:

1. A biocidal additive package comprising:
   at least one metal or metal containing compound selected from the group consisting of Cu$_2$O, Cu(OH)$_2$, Cu, CuO$_3$, Cu$_2$O$_3$, and a combination thereof, and BaCO$_3$.

2. A ceramic glaze layer comprising:
   at least one metal or metal containing compound selected from the group consisting of Cu$_2$O, Cu(OH)$_2$, Cu, CuO$_3$, Cu$_2$O$_3$, and a combination thereof, and BaCO$_3$.

3. The ceramic glaze layer according to claim 2, wherein the BaCO$_3$ is present in a ceramic glaze base in a range of at least 0.1 weight %.

4. The ceramic glaze layer according to claim 2, wherein the metallic copper or copper-containing metal compound is present in a ceramic glaze base in a range of 1 weight % to 10 weight %.

5. A biocidal ceramic article comprising:
   a substrate and
   a ceramic glaze layer on the substrate,
      wherein the ceramic glaze layer comprises at least one metal or metal containing compound selected from the group consisting of Cu$_2$O, Cu(OH)$_2$, Cu, CuO$_3$, Cu$_2$O$_3$, and a combination thereof, and BaCO$_3$.

6. The biocidal ceramic article according to claim 5, wherein the substrate is a ceramic substrate.

7. The biocidal ceramic article according to claim 5, wherein the ceramic glaze layer is a fired or cured ceramic glaze layer.

8. A method of affixing a biocidal ceramic glaze to a substrate comprising:
   providing a biocidal ceramic glazing composition having one or more biocidal agents disposed therein,
   applying the biocidal ceramic glazing composition to a substrate having a surface,
   wherein the biocidal ceramic glazing composition comprises at least one metal or metal containing compound selected from the group consisting of Cu$_2$O, Cu(OH)$_2$, Cu, CuO$_3$, Cu$_2$O$_3$, and a combination thereof, and BaCO$_3$.

9. The method according to claim 8, wherein the biocidal ceramic glazing composition is applied to a fired glaze layer on the surface of the substrate.

10. The method according to claim 8, the biocidal ceramic glazing composition is applied to an unfired glaze layer on the surface of the substrate.

* * * * *